(12) United States Patent
Minami et al.

(10) Patent No.: US 11,877,763 B2
(45) Date of Patent: Jan. 23, 2024

(54) SURGICAL TOOL WITH REDUCED ACTUATION FORCE

(71) Applicant: OLYMPUS MEDICAL SYSTEMS CORP., Tokyo (JP)

(72) Inventors: Hiroshi Minami, Chofu (JP); Hideo Sanai, Hachioji (JP); Tatsuya Suzuki, Hachioji (JP); Kirara Kono, Tachikawa (JP); Shunsuke Matsui, Hachioji (JP); Yuki Amano, Hatano (JP)

(73) Assignee: Olympus Medical Systems Corp., Tokyo (JP)

( * ) Notice: Subject to any disclaimer, the term of this patent is extended or adjusted under 35 U.S.C. 154(b) by 184 days.

(21) Appl. No.: 17/548,885

(22) Filed: Dec. 13, 2021

(65) Prior Publication Data

US 2022/0273326 A1 Sep. 1, 2022

Related U.S. Application Data

(60) Provisional application No. 63/154,372, filed on Feb. 26, 2021.

(51) Int. Cl.
*A61B 17/29* (2006.01)
*A61B 17/00* (2006.01)

(52) U.S. Cl.
CPC .... *A61B 17/2909* (2013.01); *A61B 2017/00367* (2013.01); *A61B 2017/00845* (2013.01); *A61B 2017/291* (2013.01); *A61B 2017/2902* (2013.01); *A61B 2017/2904* (2013.01); *A61B 2017/2916* (2013.01); *A61B 2017/2919* (2013.01)

(58) Field of Classification Search
CPC ........ A61B 2017/2919; A61B 17/2909; A61B 17/00234; A61B 17/29; A61B 2017/00845; A61B 2017/2912; A61B 2017/2916; A61B 17/320016; A61B 2017/00367; A61B 2017/2902; A61B 17/320092; A61B 2017/320092; A61B 2017/291
USPC ........................................ 606/205
See application file for complete search history.

(56) References Cited

U.S. PATENT DOCUMENTS

| | | | | |
|---|---|---|---|---|
| 5,954,746 | A | * | 9/1999 | Holthaus ........ A61B 17/320092 606/174 |
| 2006/0060630 | A1 | * | 3/2006 | Shelton ............ A61B 17/07207 227/19 |
| 2006/0217742 | A1 | * | 9/2006 | Messerly ........... A61B 17/1285 606/139 |

(Continued)

*Primary Examiner* — Timothy J Neal
*Assistant Examiner* — Mitchell Brian Hoag
(74) *Attorney, Agent, or Firm* — Morgan, Lewis & Bockius LLP

(57) ABSTRACT

A surgical tool including a housing having a proximal end and a distal end, a yoke disposed within the housing between the proximal end and the distal end, a handle pivotally coupled to the housing, and a pivot assembly coupling the yoke to the housing. The pivot assembly includes a first link having a first end and a second end. The first end of the first link is rotatably coupled to the housing and the second end of the first link rotatably coupled to a second link at a first end of the second link. The second link has a second end rotatably coupled to the yoke. The handle is coupled to the pivot assembly such that movement of the handle causes movement of the yoke.

17 Claims, 12 Drawing Sheets

(56) References Cited

U.S. PATENT DOCUMENTS

| | | | |
|---|---|---|---|
| 2007/0123933 A1* | 5/2007 | Johnson | A61B 17/2909 606/205 |
| 2011/0087218 A1* | 4/2011 | Boudreaux | A61B 18/1445 606/208 |
| 2015/0082928 A1* | 3/2015 | Kappus | A61B 17/29 74/103 |
| 2016/0174978 A1* | 6/2016 | Overmyer | A61B 17/07207 227/178.1 |
| 2016/0262782 A1* | 9/2016 | Kalmann | A61B 17/282 |
| 2017/0055970 A1* | 3/2017 | Hess | A61B 17/2909 |
| 2018/0296213 A1* | 10/2018 | Strobl | A61B 18/1445 |
| 2019/0053809 A1* | 2/2019 | Chang | A61B 17/1285 |
| 2020/0038041 A1* | 2/2020 | Chu | A61B 17/221 |
| 2020/0046217 A1* | 2/2020 | Butcher | A61B 1/31 |
| 2020/0046363 A1* | 2/2020 | Baril | A61B 17/128 |
| 2021/0186034 A1* | 6/2021 | Frea | A21D 13/41 |

* cited by examiner

SURGICAL TOOL WITH REDUCED ACTUATION FORCE

RELATED APPLICATION DATA

This application is based on and claims priority under 35 U.S.C. § 119 to U.S. Provisional Application No. 63/154,372, filed Feb. 26, 2021, the entire contents of which are incorporated herein by reference.

FIELD OF THE INVENTION

The present invention generally relates to a surgical tool having a reduced actuation force, and more particularly, a surgical tool having a handle requiring a reduced actuation force for actuating a grasping instrument.

BACKGROUND OF THE INVENTION

Surgical tools that grip and/or cut tissue by squeezing a handle, such as laparoscopic surgical tools, may be actuated by movement of a yoke. For example, hand-held surgical tools are commonly used by surgeons for minimally invasive, robotic, and open surgeries. These surgical tools may include an end instrument assembly that is actuated by a handle that the surgeon squeezes. However, these tools often require significant force on the handle to actuate the yoke that in turn actuates a grasper assembly disposed at the end of the tool. Further, the mechanisms required to transmit the force from the handle to actuate the grasper assembly can be bulky and require significant space within the housing of the tool.

BRIEF SUMMARY OF THE INVENTION

Embodiments of the present invention are directed to a surgical tool having a housing having a proximal end and a distal end, a yoke disposed within the housing between the proximal end and the distal end, a handle pivotally coupled to the housing, and a pivot assembly coupling the yoke to the housing. The pivot assembly may include a first link having a first end and a second end, the first end of the first link rotatably coupled to the housing and the second end of the first link rotatably coupled to a second link at a first end of the second link, the second link having a second end rotatably coupled to the yoke. The handle may be coupled to the pivot assembly such that movement of the handle causes movement of the yoke.

In some embodiments, the surgical tool further includes a pivot pin pivotably coupling the second end of the first link to the first end of the second link, and a slot disposed within in the handle configured to slidably receive the pivot pin.

In some embodiments, the slot includes a proximal end and a distal end, the pivot pin being proximate to the proximal end of the slot when the handle is in an initial position and the pivot pin being proximate the distal end of the slot when the handle is in an actuated position. The proximal end of the slot may be disposed above the distal end of the slot. The slot may be curved and extends from the proximal end of the slot to the distal end of the slot. The slot may be downwardly curved towards the handle. The slot may be upwardly curved towards the yoke.

In some embodiments, the pivot pin includes a ring contacting an inner surface of the slot. The slot may include a low-friction coating formed on a region of the slot where the pivot pin contacts the slot.

In some embodiments, the pivot pin includes a first end and a second end, each of the first end and the second end being tapered. The pivot pin may be disposed through the handle, the first link, and the second link.

In some embodiments, the handle is coupled to the housing at a pivot point, the pivot pin being disposed closer to a bottom of the handle than the pivot point. The pivot pin may be disposed between the first link and the second link. Pivoting of the handle towards the proximal end of the housing may move the yoke distally.

In some embodiments, the handle has an initial position and an actuated position, the actuated position being when the handle is disposed proximate the proximal end of the housing compared to when the handle is in the initial position. The handle may be coupled to one or both of the first link and the second link.

In some embodiments, first link and the second link form an angle, the angle increasing as the yoke moves towards the distal end. The first link may be disposed distal to the second link. The second end of the first link may be rotatably coupled to the first end of the second link by a pivot pin disposed through the handle. The second end of the second link may be rotatably coupled to the yoke by a second pivot pin disposed through the yoke. The first end of the second link may be rotatably coupled to the housing by a third pivot pin disposed through the housing.

In some embodiments, surgical tool further includes a grasper instrument disposed at a distal end of the housing, wherein movement of the handle results in movement of the yoke causing actuation of the grasper instrument.

In some embodiments, the pivot assembly includes a motor coupled to the yoke and configured to move the yoke. A maximum length of the pivot assembly may be less than or equal to approximately 20 mm.

In some embodiments, the housing includes a longitudinal axis extending from the proximal end to the distal end, the handle and the yoke configured to move along the longitudinal axis.

In some embodiments, the surgical tool further includes an elongated shaft extending from the distal end of the housing, and a grasping instrument disposed on a distal end of the elongated shaft, the grasping instrument coupled to the yoke such that movement of the yoke causes actuation of the grasping instrument.

Another embodiment of the present invention may provide a surgical tool having a housing having a proximal end and a distal end, a yoke disposed within the housing, a handle having a top and bottom, the handle pivotally coupled to the housing at a pivot point, the handle having a slot that is curved, wherein pivoting of the handle causes the yoke to move proximally and distally, and a pivot assembly coupling the yoke to the housing, the pivot assembly including a first link having a first end and a second end, the first end of the first link rotatably coupled to the housing and the second end of the first link rotatably coupled to a second link by a pivot pin at a first end of the second link, the second link having a second end rotatably coupled to the yoke, and the pivot pin disposed through the slot to couple the handle to the pivot assembly. The pivot pin may be disposed closer to the bottom of the handle than the pivot point.

Another embodiment of the present invention may provide a laparoscopic surgical tool having a housing having a proximal end and a distal end, the housing including a shaft extending from a portion of the housing proximate the proximal end to the distal end, a yoke disposed within the housing, the yoke slidable relative to the housing, a handle having a top and a bottom, the handle pivotally coupled to the housing at a pivot point, the handle having a slot that is curved, wherein pivoting of the handle causes the yoke to move proximally and distally, a grasper instrument disposed at the distal end of the housing, the grasper instrument configured to actuate upon movement of the yoke, a grip disposed proximate to the distal end compared to the handle, and a pivot assembly coupling the yoke to the housing, the pivot assembly including a first link having a first end and a second end, the first end of the first link rotatably coupled to the housing and the second end of the first link rotatably coupled to a second link by a pivot pin at a first end of the second link, the second link having a second end rotatably coupled to the yoke, the pivot pin being disposed closer to the bottom of the handle than the pivot point and being disposed through the slot to couple the handle to the pivot assembly. The first link and the second link may form an angle and actuation of the handle may increase the angle to drive the yoke towards the distal end.

BRIEF DESCRIPTION OF THE SEVERAL VIEWS OF THE DRAWINGS

The foregoing summary, as well as the following detailed description of embodiments of the surgical tool, will be better understood when read in conjunction with the appended drawings of exemplary embodiments. It should be understood, however, that the invention is not limited to the precise arrangements and instrumentalities shown.

DETAILED DESCRIPTION OF THE EXEMPLARY EMBODIMENTS OF THE INVENTION

Figure 1:
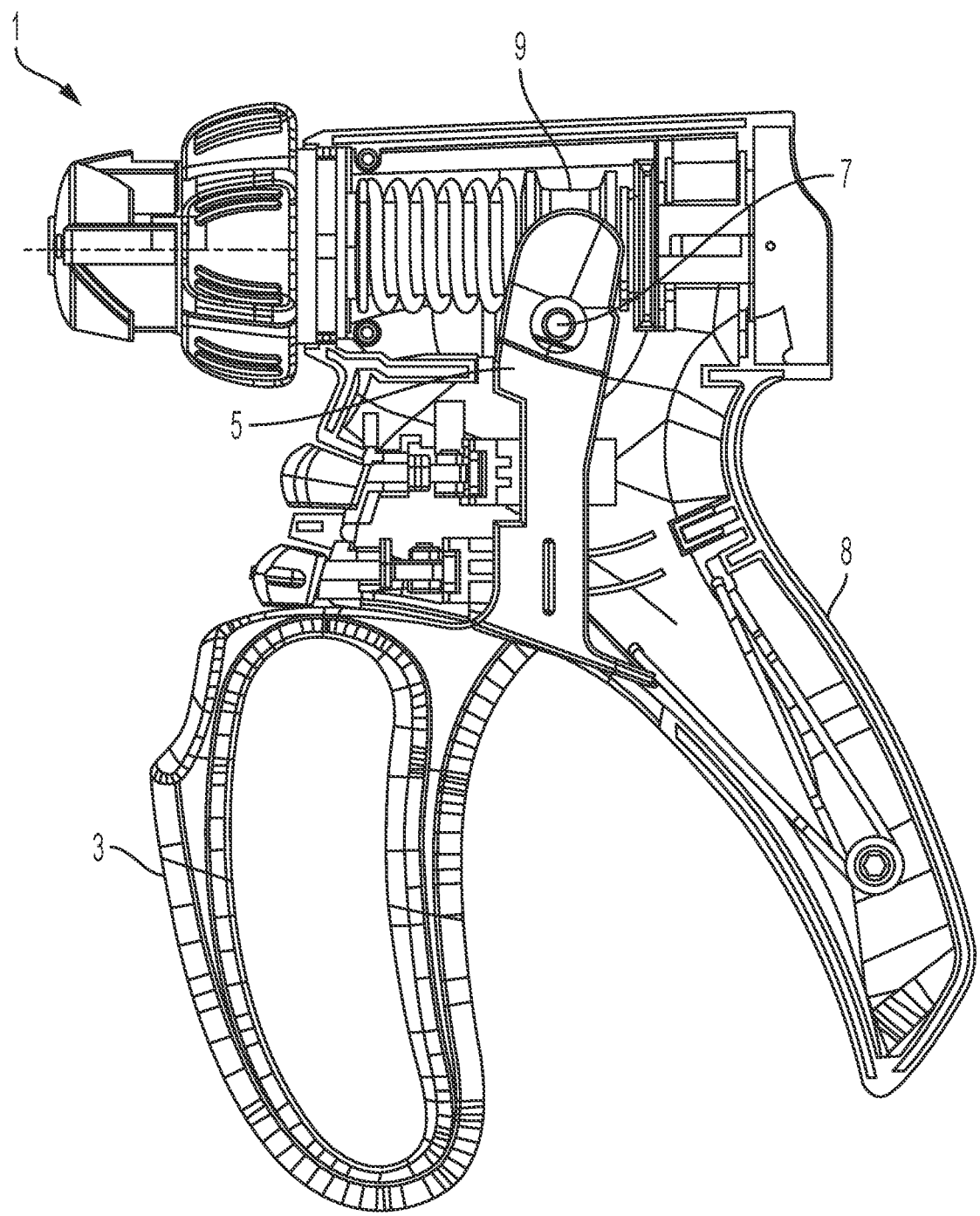
FIG. 1 is a partial cross-sectional view of a prior art open jaw surgical tool.
Figure 2:
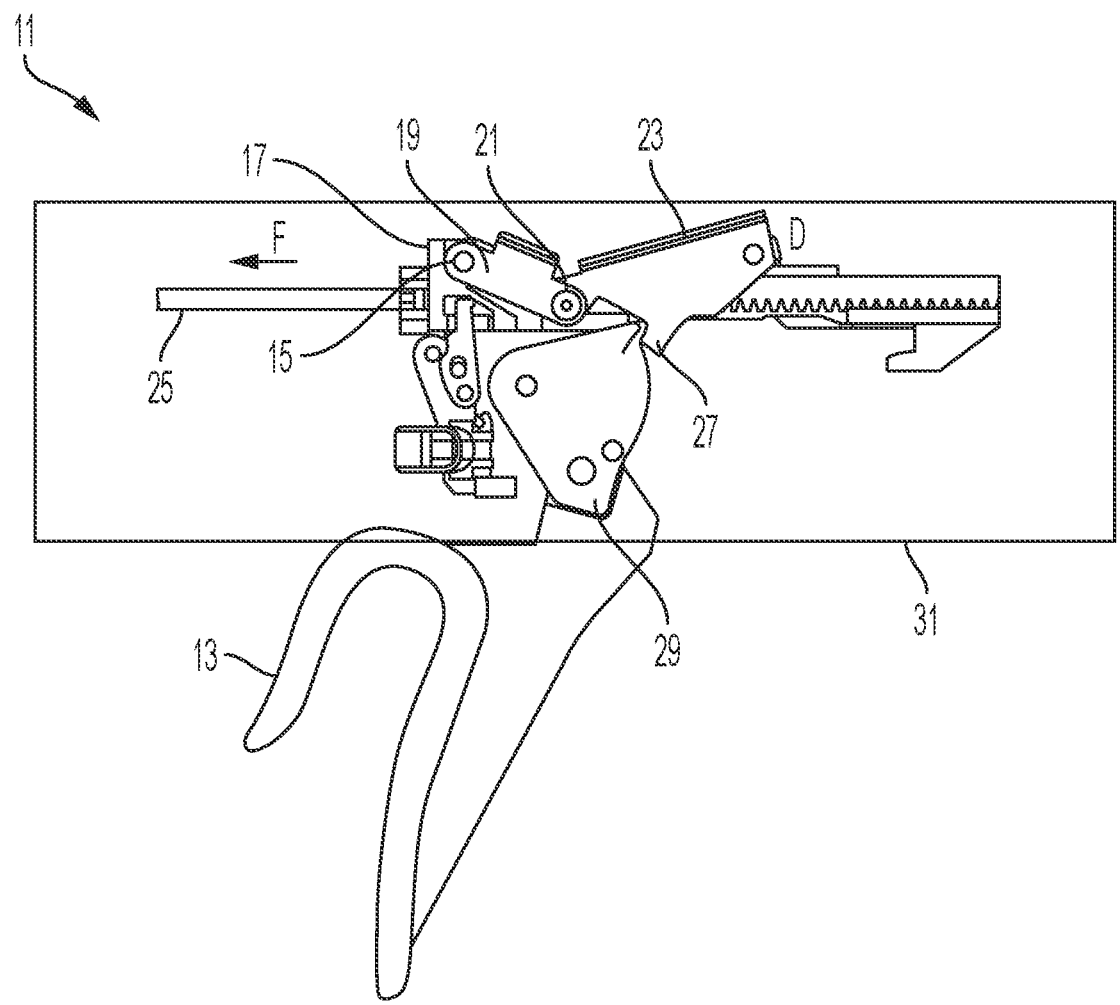
FIG. 2 is a side view of some interior components of another prior art surgical tool.

Referring to FIGS. 1-2, existing surgical tools for laparoscopic procedures include handles that actuate a yoke to perform specific functions, such as actuating a grasping instrument, based on movement of the yoke. The grasping instrument may be disposed at the end of the surgical tool. These surgical tools may be hand-held tools configured to grasp and cut tissue.

As shown in FIG. 1, a known surgical tool 1 may include handle 3, coupling member 5, pivot point 7, grip 8, and slider 9. In some embodiments, surgical tool 1 is configured grasp tissue and/or cut tissue using handle 3 and a grasping instrument (not shown). In some embodiments, grip 8 is configured to be held in the hand of a user (e.g., surgeon or other operator), and a handle 3 is movable relative to grip 8. Handle 3 may be coupled to pivot point 7 via coupling member 5. Handle 3 may be actuated by a user and configured to pivot about pivot point 7 to move slider 9. For example, handle 3 may be coupled to slider 9 and may be actuated by a user such that moving handle 3 results in movement of slider 9. Movement of slider 9 may actuate the grasping instrument disposed at the distal end of surgical tool 1. Grasping instrument may be configured to open and close by actuation of handle 3 relative to grip 8. In some embodiments, the gripping force required to fully actuate handle 3 is large. For example, the gripping force required to fully actuate handle 3 and move slider 9 may be greater than 30 Newtons (N).

As shown in FIG. 2, a known surgical tool 11 may include housing 31, handle 13, first link 23, second link 19, third link 29, yoke 17, and pivot pin 21. Handle 13 may be coupled to third link 29, which may be configured to actuate first link 23 via cam 27. First link 23 may be coupled to second link 19 via pivot pin 21 and first link 23 may be further coupled to yoke 17. Similar to surgical tool 1, surgical tool 11 may be a hand-held surgical tool configured to actuate a grasping instrument. For example, in use, a user may apply a gripping force to handle 13. The gripping force on handle 13 is then translated to movement of the grasping instrument disposed at a distal end of surgical tool 11. In some embodiments, surgical tool 11 is configured grasp tissue and/or cut tissue using handle 13 and the grasping instrument. In use, actuation of handle 13 results in third link 29 moving second link 19, which results in movement of first link 23, thereby moving yoke 17. Yoke 17 may be attached to the grasper instrument (not shown) or another tool disposed at the distal end of shaft 25. The gripping force required to fully actuate handle 13 and move yoke 17 may be greater than 30 N. In some embodiments, first link 23, second link 19, and third link 29 require significant space within housing 31.

Referring to FIGS. 3A-8, there is shown tool 100 having an improved pivot assembly for translating a gripping force applied to a handle to actuation of an end instrument, such as a grasping instrument as shown. In use, tool 100 may be used to actuate an instrument disposed on the tool. The improved pivot assembly of tool 100 may better translate the gripping force applied to the handle to actuate the instrument. For example, the improved pivot assembly may require a reduced gripping force on the handle of tool 100 to cause actuation of the instrument compared to known surgical tools. Tool 100 may be configured to better translate movement of the handle to movement of the instrument. In some embodiments, tool 100 is configured to translate squeezing (e.g., pivoting) of a handle to axial movement of a yoke, which is coupled to the instrument. Movement of the yoke may result in actuation of the instrument.

In some embodiments, tool 100 is a surgical tool used for grasping, manipulating, and cutting tissue. For example, tool 100 may be a surgical energy device having a grasping instrument configured to grasp, manipulate, and cut/cauterize tissue. The grasping instrument may be coupled to an elongated narrow shaft extending from the housing of tool 100 and may be configured to be inserted within a patient, while a substantial portion of the housing of tool 100 remains outside the patient. The shaft of the open jaw may be inserted within the patient and the elongated shaft may include the grasping instrument that is configured to open and close to grasp tissue.

In some embodiments, tool 100 is configured to grasp and/or cut tissue disposed within small, confined areas. For example, movements of the user's hand on the handle may be translated into corresponding movements of the grasping instrument when used during surgery. In some embodiments, tool 100 is a laparoscopic tool used to grasp and cut tissue during a laparoscopic procedure. However, tool 100 may be a surgical tool used for open surgeries, robotic surgeries, or minimally invasive surgeries. Tool 100 may also be used for non-surgical applications. For example, tool 100 may be used in applications such as automotive, construction, cleaning, manufacturing, non-surgical medical procedures, or any other application desired. Tool 100 may be used for any application requiring translation of a force applied to a handle to actuation of an instrument. In some embodiments, tool 100 is configured to be hand-held by a user.

Figure 3A:
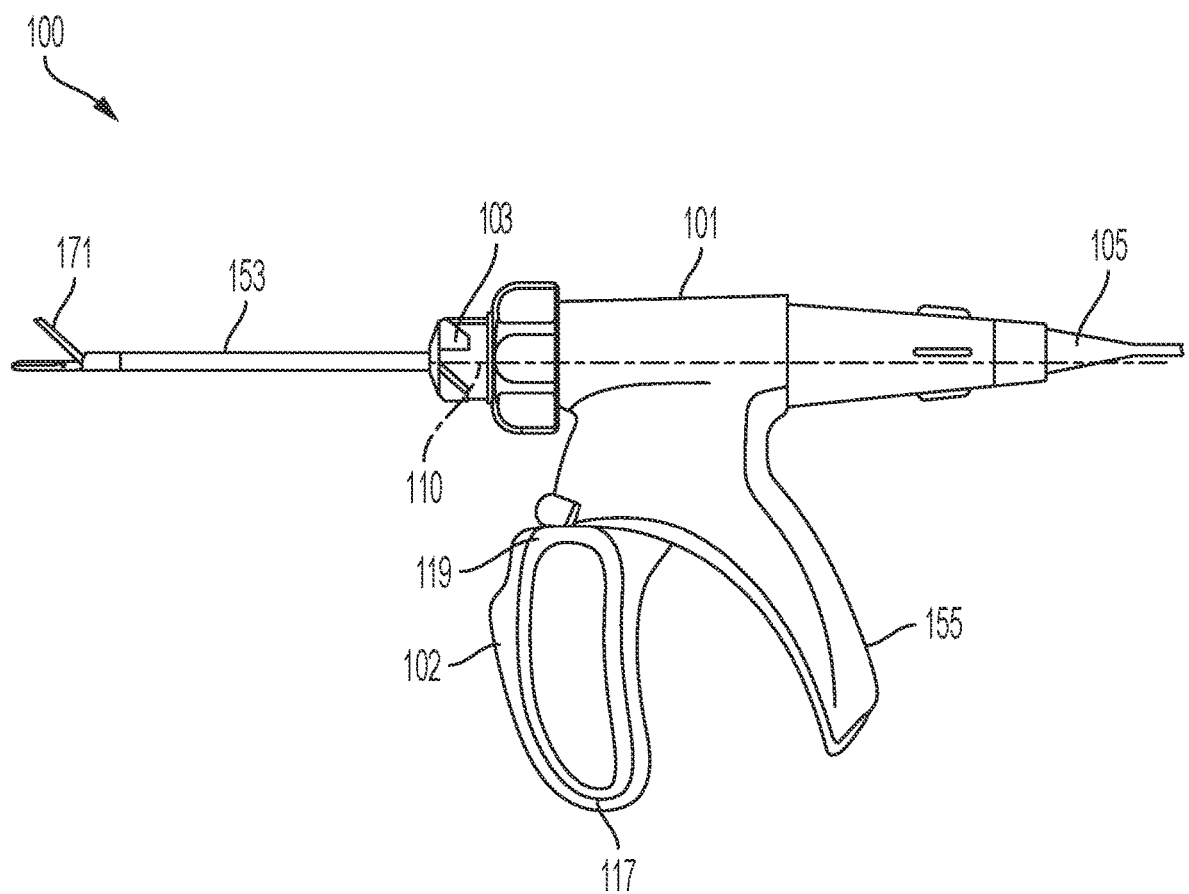
FIG. 3A is a side view of a laparoscopic surgical tool having a grasping instrument in accordance with an exemplary embodiment of the present invention shown in an open configuration.
Figure 3B:
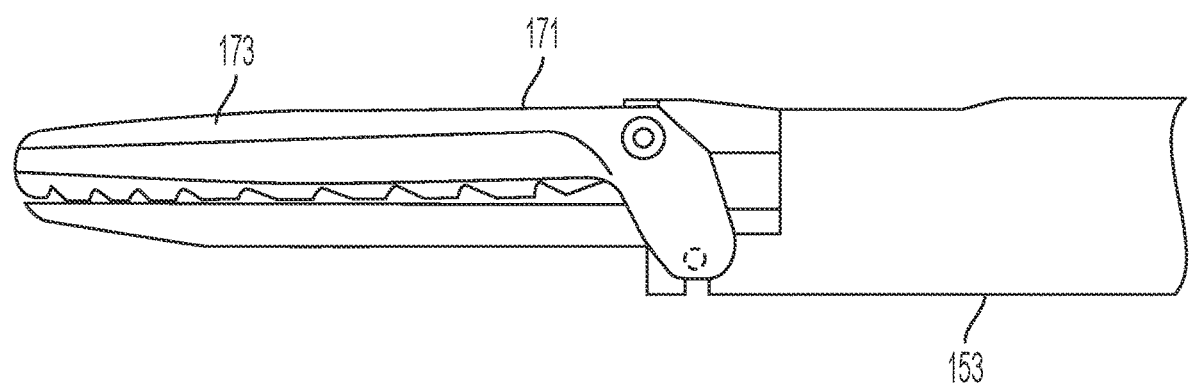
FIG. 3B is zoomed-in view of the grasping instrument of FIG. 3A shown in a closed configuration.
Figure 3C:
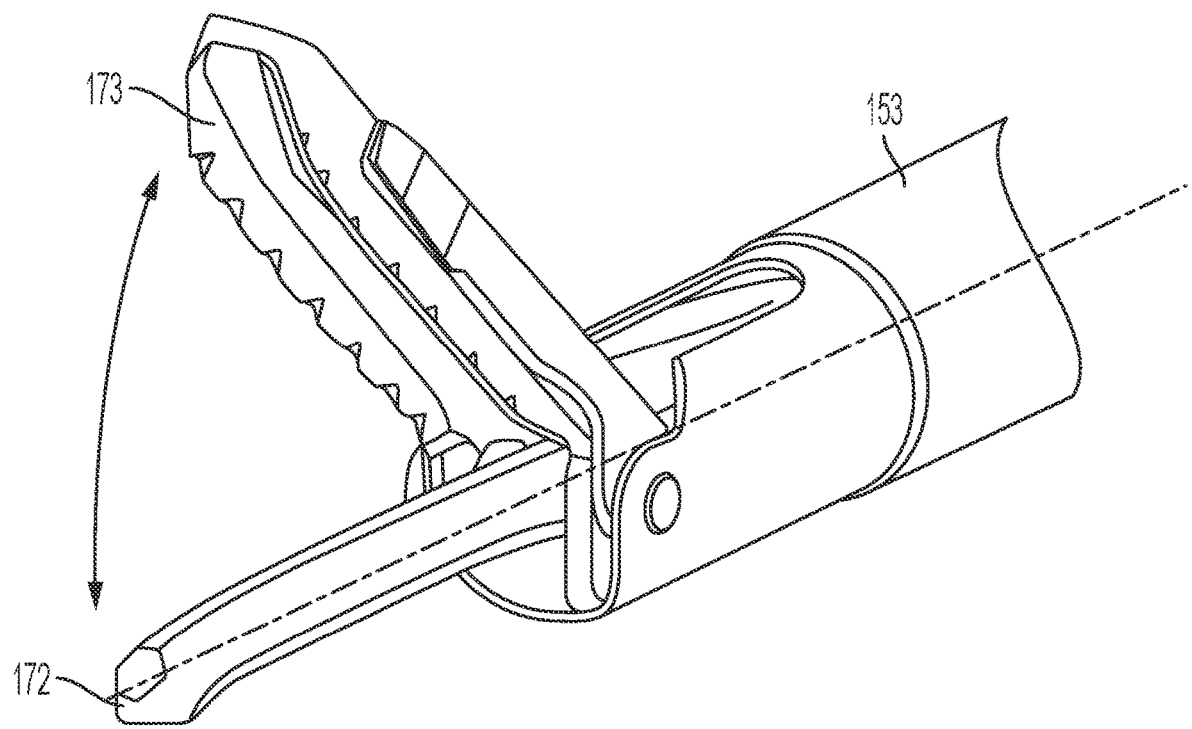
FIG. 3C is zoomed-in view of the grasping instrument of FIG. 3A in an open configuration.

Referring to FIGS. 3A-3C, tool 100 may include housing 101, handle 102, shaft 153, grip 155, and instrument assembly 171. Handle 102 may be actuated by a user to actuate instrument assembly 171. For example, handle 102 may have an initial position and an actuated position. The actuated position may be when handle 102 moved relative to grip 155 such that handle 102 is proximate to grip 155 compared to when handle 102 is in the initial position. In use, a user may hold tool 100 by placing grip 155 within their palm and placing their thumb around grip 155. The user's fingers may be wrapped around handle 102 and the user may squeeze their hand, bring their fingers towards their palm and thumb, to pull handle 102 towards grip 155 to actuate handle 102. Actuation of handle 102 may actuate instrument assembly 171. In some embodiments, handle 102 includes a loop and the user's fingers are disposed through the loop during use. However, handle 102 may include no loop, an open loop, finger loops for each finger, a lever, or a trigger to be actuated by a one or more fingers.

In some embodiments, handle 102 is biased to be in the initial position and must be moved by a user or motor to the actuated position. Moving handle 102 to the actuated position may result in actuation of instrument assembly 171. In some embodiments, instrument assembly 171 is a grasping/open jaw instrument and includes a closed (FIG. 3B) and open (FIG. 3C) configuration.

Referring to FIG. 3A, housing 101 may include proximal end 105 and distal end 103. In some embodiments, housing includes longitudinal axis 110 that extends from proximal end 105 through distal end 103 and down shaft 153. Shaft 153 may extend from distal end 103 of housing 101 and instrument assembly 171 may be located at a distal end of shaft 153. In some embodiments, instrument assembly 171 is a grasping instrument. For example, instrument assembly 171 may include jaw 173 and blade 172. Jaw 173 may be movable relative to blade 172 between a closed configuration (FIG. 3B) and an open configuration (FIG. 3C). Blade 172 may be configured to cut and/or cauterize tissue disposed within instrument assembly 171. For example, jaw 173 may be configured to grasp tissue or a vessel and blade 172 may be configured to cut and/or cauterize the tissue or vessel. Blade 172 may be configured to receive electrical current such that it heats up to cauterize tissue. In some embodiments, instrument assembly 171 includes scissors, forceps, needle drivers, retractors, syringes, tubing for suction and/or irrigation, blades/knifes, and/or cauterizing or energy instruments. However, instrument assembly 171 may be any instrument desired. For example, instrument assembly 171 may be an instrument used for medical, automotive, construction, cleaning, manufacturing, or any other application desired.

As shown in FIGS. 4A-8, tool 100 may include handle 102, yoke 106, and pivot assembly 115. Yoke 106 and pivot assembly 115 may be disposed within housing 101. For example, yoke 106 and pivot assembly 115 may be coupled to housing 101. In some embodiments, handle 102 is coupled to housing 101. Handle 102 may be additionally coupled to housing 101 and yoke 106 via pivot assembly 115. In some embodiments, yoke 106 is disposed along longitudinal axis 110 and between proximal end 105 and distal end 103. Yoke 106 may be disposed along longitudinal axis 110 and axially aligned with shaft 153. In some embodiments, yoke 106 is coupled to instrument assembly 171 via shaft 153 such that movement of yoke 106 along longitudinal axis 110 causes actuation of instrument assembly 171.

In some embodiments, yoke 106 is coupled to housing 101 to allow yoke 106 to move axially along longitudinal axis 110. For example, yoke 106 may be slidably coupled to housing 101 such that yoke 106 is configured to move along longitudinal axis 110 from proximal end 105 to distal end 103. Yoke 106 may also be configured to move axially in alignment with shaft 153. In some embodiments, yoke 106 is coupled to housing 101 along a track to allow yoke 106 to move axially along longitudinal axis 110. However, yoke 106 may be coupled to housing 101 via other methods, such as via magnets, rails, wheels, biasing elements, springs, tension members, or any other method desired. Movement of yoke 106 along longitudinal axis 110 may result in actuation of instrument assembly 171.

In some embodiments, yoke 106 includes protrusion 109 and housing 101 includes inside track 111 and an outside track (not shown). Track 111 may be configured to receive protrusion 109 such that yoke 106 is slidable relative to housing 101. For example, yoke 106 may be slidable along inside track 111 and/or the outside track such that yoke 106 is slidable along longitudinal axis 110 relative to housing 101. In some embodiments, protrusion 109 is configured to rest on inside track 111 and/or the outside track such that protrusion 109 and yoke 106 is slidable along one or more of inside track 111 or the outside track. In some embodiments, inside track 111 includes stopping portion 113 to prevent yoke 106 from moving too far back towards proximal end 105. Inside track 111 and/or the outside track may be configured to allow yoke 106 to move along longitudinal axis 110 from distal end 103 to proximal end 105.

In some embodiments, handle 102 is coupled and secured to housing 101. Handle 102 may be configured to move from the initial position (FIG. 4A) to the actuated position (FIG. 4B). The actuated position may be when handle 102 is proximate proximal end 105 compared to when handle 102 is in the initial position. In some embodiments, the initial position of handle 102 is when handle 102 has not been actuated by a user. The initial position of handle 102 may be when handle 102 is at rest and yoke 106 is disposed proximate proximal end 105 compared to when handle 102 is actuated. In some embodiments, the force required to move handle 102 from the initial position (FIG. 4A) to the actuated position (FIG. 4B) is approximately 30 N or less. For example, the force required to move handle 102 from the initial position to the actuated position may be less than 35 N. In some embodiments, the axial force required to move handle 102 from the initial position to the actuated position is approximately 150 N or less. The axial force may be the force that is applied along longitudinal axis 110. For example, the axial force may be the force the drives yoke 106 from proximal end 105 to distal end 103. In some embodiments, the axial force drives yoke 106 along longitudinal axis 110. In other words, the axial force is the force transmitted through shaft 153 to actuate instrument assembly 171, such as jaw 173. In some embodiments, when an axial force is transmitted to jaw 173 via yoke 106, jaw 173 rotates around a pivot point connected to shaft 153 resulting in jaw 173 closing. The direction of the axial force coincides with the direction of shaft 153.

Figure 4A:
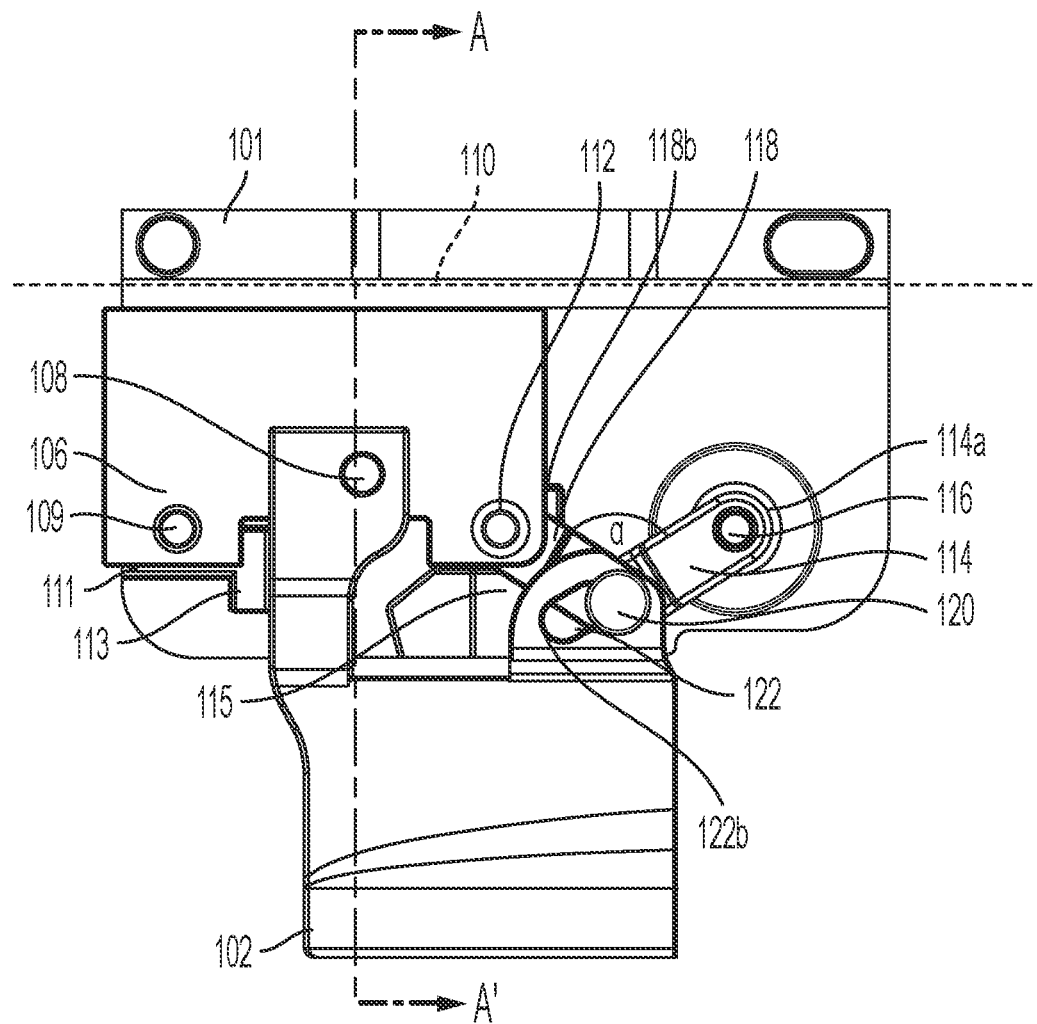
FIG. 4A is a partial side view of the pivot assembly of the surgical tool of FIG. 3A shown in an initial position and with the housing and handle removed for demonstrative purposes.
Figure 4B:
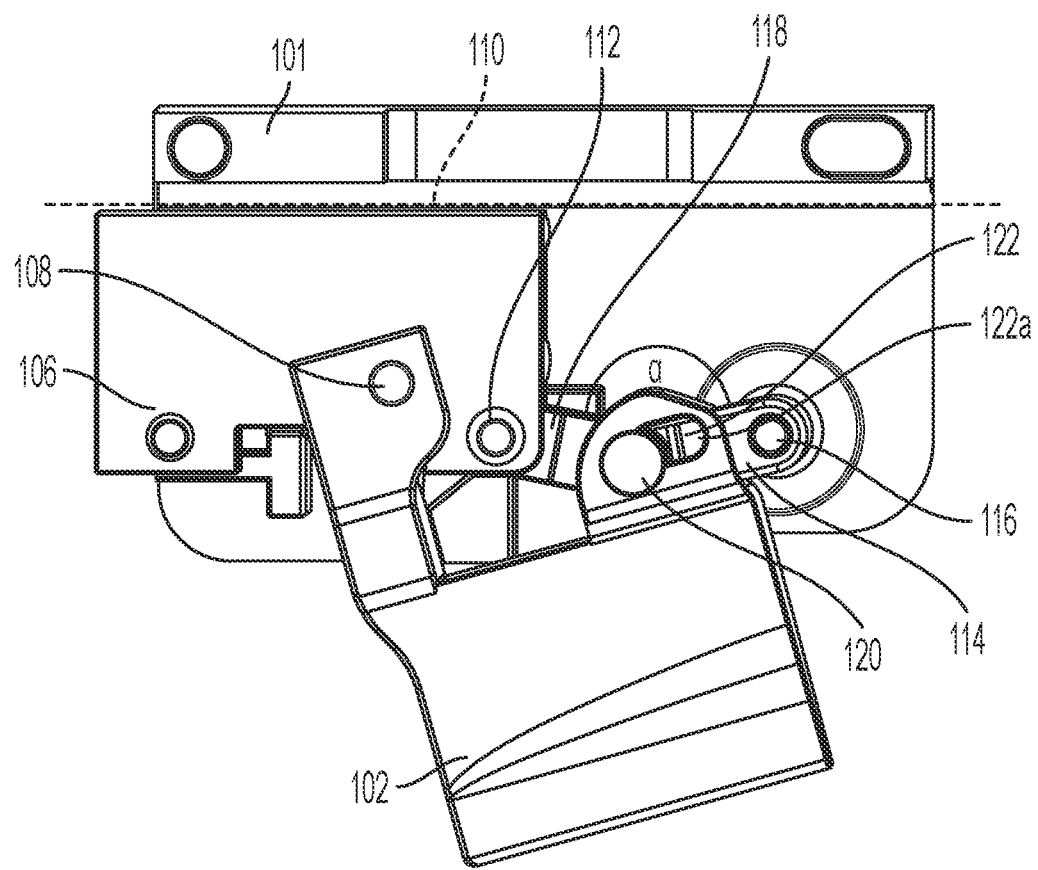
FIG. 4B is a partial side view of the pivot assembly of FIG. 4A shown in an actuated position.

Referring to FIGS. 3A and 4A-4B, handle 102 may be pivotally coupled to housing 101. In some embodiments, handle 102 is coupled to housing 101 via pivot point 108. For example, handle 102 may be configured to rotate or pivot about pivot point 108. In some embodiments, when handle 102 moves from the initial position to the actuated position, handle 102 pivots about pivot point 108 towards distal end 103, and yoke 106 is driven forward towards distal end 103 of housing 101 via pivot assembly 115.

In some embodiments, driving of yoke 106 results in actuation of instrument assembly 171. For example, instrument assembly 171 may be coupled to yoke 106 via shaft 153. In some embodiments, driving of yoke 106 proximally and distally causes jaw 173 of instrument assembly 171 to open and close. For example, moving handle 102 from the initial position to the actuated position may result in driving yoke 106 towards distal end 103 thereby causing jaw 173 to close. Movement of handle 102 from the actuated position back to the initial position may cause yoke 106 to move proximally, causing jaw 173 to open. However, instrument assembly 171 may be any instrument desired such that movement of handle 102 and yoke 106 causes actuation of instrument assembly 171.

In some embodiments, handle 102 and yoke 106 may each have a stroke length. The stroke length may be the length of the movement required to fully actuate handle 102 or full length of movement of yoke 106. In some embodiments, handle 102 may have a stroke length between approximately 5 mm and approximately 25 mm. In a preferred embodiment, handle 102 has a stroke length between 9 mm and 14 mm. In some embodiments, yoke 106 may have a stroke length between approximately 1 mm and approximately 20 mm. In a preferred embodiment, yoke 106 has a stroke length between approximately 3 mm and approximately 5 mm.

In some embodiments, handle 102 is coupled to yoke 106 via pivot assembly 115. Pivot assembly 115 may be configured to drive yoke 106 proximally and distally upon movement of handle 102. Pivot assembly 115 may be sized and shaped to be entirely disposed within housing 101. For example, pivot assembly 115 may not extend into grip 155 and may have a maximum length of less than or equal to 20 mm.

Referring to FIGS. 4A-4B, pivot assembly 115 may include first link 114 and second link 118. First link 114 may have first end 114a and second end 114b, and second link 118 may have first end 118a and second end 118b. First end 114a of first link 114 may be coupled to housing 101. In some embodiments, first end 114a is rotatably coupled to housing 101. First end 114a may be coupled to housing 101 via first pivot pin 116. First end 114a may be pivotably coupled to housing 101 such that first end 114a is fixed in location relative to housing 101 and is only configured to pivot about first pivot pin 116. Second end 114b of first link 114 may be coupled to first end 118a of second link 118. In some embodiments, second end 114b is pivotably coupled to first end 118a via second pivot pin 120. Second end 118b of second link 118 may be pivotably coupled to yoke 106 at third pivot pin 112. In some embodiments, second pivot pin 120 and third pivot pin 112 are configured to move relative to housing 101. For example, third pivot pin 112 and second pivot pin 120 may be configured to move proximally and distally and away and towards handle 102. Second pivot pin 120 and third pivot pin 112 being movable relative to housing 101 results in second 114a of first link 114 and first end 118a and second end 118b of second link 118 being movable relative to housing 101.

In some embodiments, each of first pivot pin 116, second pivot pin 120, and third pivot pin 112 extend through housing 101. Third pivot pin 112 may extend through both yoke 106 and housing 101. For example, third pivot pin 112 may extend through the width of yoke 106 and housing 101. In some embodiments, second pivot pin 120 is disposed between first pivot pin 116 and third pivot pin 112.

Referring to FIGS. 3A and 4A, second pivot pin 120 may be disposed lower than pivot point 108. For example, second pivot pin 120 may be disposed proximate to handle 102 and further away from yoke 106 compared to pivot point 108. Further, second pivot pin 120 may be disposed proximate to where a user contacts handle 102 compared to first pivot pin 116 and third pivot pin 112. In some embodiments, handle 102 includes top 119 and bottom 117. Second pivot pin 120 may be disposed closer to bottom 117 than pivot point 108. For example, pivot point 108 may be disposed higher than second pivot pin 120 resulting in second pivot pin 120 being disposed closer to bottom 117 of handle 102. Pivot point 108 being disposed higher than second pivot pin 120 may result in the distance between the gripping force applied to handle 102 and pivot point 108 being greater than the distance between the gripping force applied to handle 102 and second pivot pin 120. In some embodiments, pivot point 108 overlaps with yoke 106. For example, pivot point 108 may be adjacent to yoke 106 such that pivot point 108 overlaps with yoke 106 and second pivot pin 120 may not.

In some embodiments, placing pivot point 108 higher than second pivot pin 120 results in a reduction in the gripping force required to actuate handle 102. In practice, placing pivot point 108 above second pivot pin 120 changes the direction that handle 102 is moved compared to existing conventional surgical tools, thereby reducing the force required to actuate handle 102. In some embodiments, first pivot pin 116, second pivot pin 120, and third pivot pin 112 are disposed below pivot point 108.

In some embodiments, first link 114 and second link 118 each have a length greater than their width. In some embodiments, first link 114 and second link 118 have the same length and width. However, first link 114 may have a different length and width than second link 118. First link 114 may have a length of approximately 72 mm and a width of approximately 23 mm. However, first link 114 may have a length between approximately 25 mm and approximately 100 mm and a width between approximately 10 mm and 50 mm. Second link 118 may have a length of approximately 72 mm and a width of approximately 23 mm. However, second link 118 may have a length between approximately 25 mm and approximately 100 mm and a width between approximately 10 mm and 50 mm. In some embodiments, first link 114 and/or second link 118 are comprised of polycarbonate or polyacetal. First link 114 and second link 118 may be sized and shaped to fit within a small confined area of housing 101, thereby reducing the amount of space required for pivot assembly 115.

In some embodiments, pivot assembly 115 includes first pivot pin 116, second pivot pin 120, and third pivot pin 112. First pivot pin 116 may have a diameter of approximately 4 mm, second pivot pin 120 may have a diameter of approximately 4 mm, and third pivot pin 112 may have a diameter of approximately 4 mm. First pivot pin 116, second pivot pin 120, and third pivot pin 112 may have a length of approximately 16 mm. However, first pivot pin 116, second pivot pin 120, and third pivot pin 112 may have a length between approximately 5 mm and approximately 25 mm. First pivot pin 116, second pivot pin 120, and third pivot pin 112 may have a diameter of approximately 4 mm. However, first pivot pin 116, second pivot pin 120, and third pivot pin 112 may have a diameter between approximately 1 mm and approximately 10 mm. In some embodiments, first pivot pin 116, second pivot pin 120, and third pivot pin 112 each have a different diameter. Each of first pivot pin 116, second pivot pin 120, and third pivot pin 112 may be received through housing 101 via apertures disposed within housing 101. In some embodiments, each of first pivot pin 116, second pivot pin 120, and third pivot pin 112 extends through a substantial width of housing 101.

Figure 5:
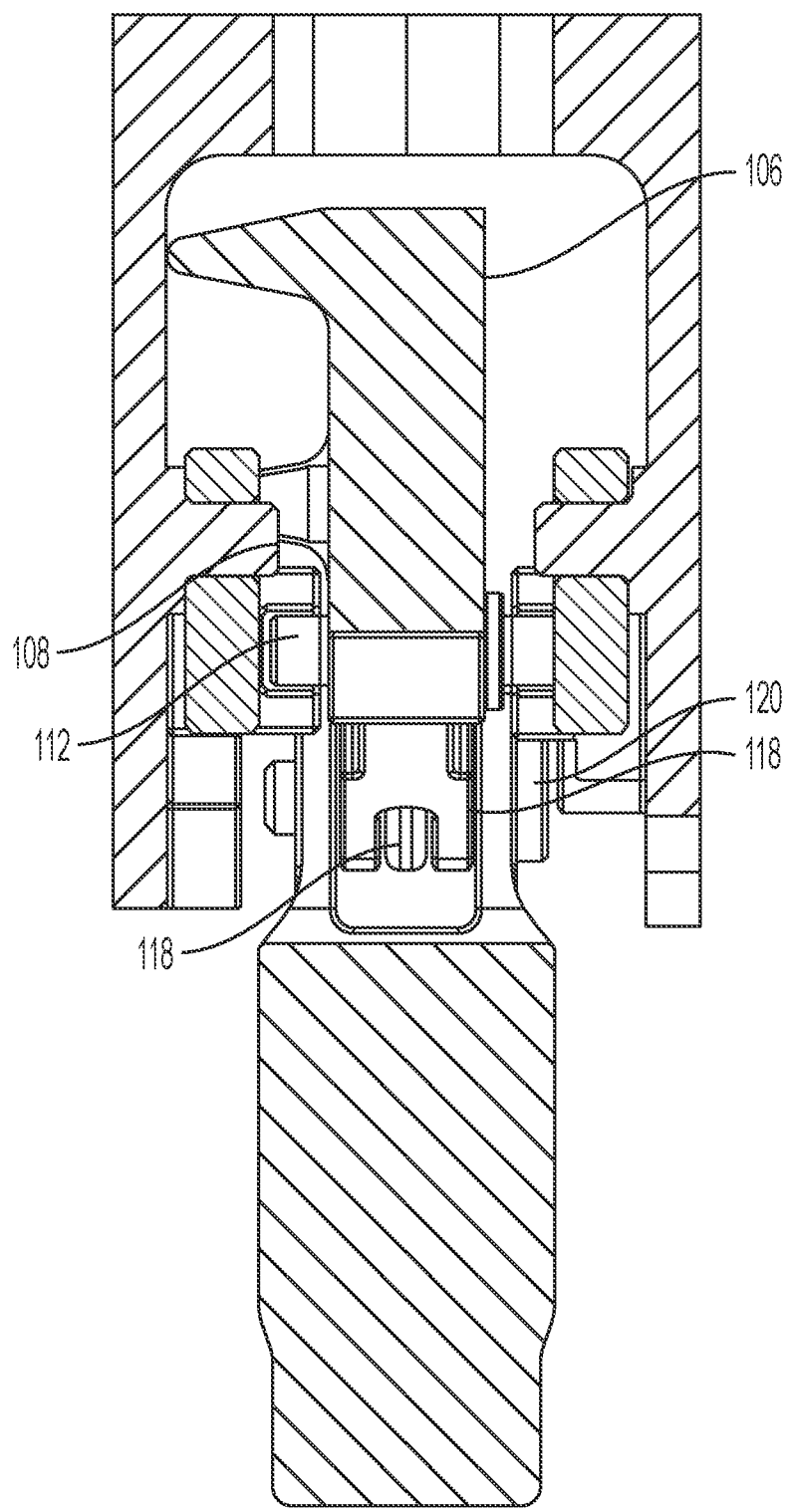
FIG. 5 is a cross-sectional front view of an exemplary pivot assembly of FIG. 4A taken along line A-A'.

Referring to FIGS. 4A-5, second pivot pin 120 may be disposed through second end 114b of first link 114 and first end 118a of second link 118. First link 114 and second link 118 may form angle α when coupled together by second pivot pin 120. In some embodiments, first link 114 may be disposed at angle α relative to second link 118. Movement of second pivot pin 120 may result in movement of first link 114 and second link 118, which may increase or decrease angle α. For example, movement of second pivot pin 120 upwards, toward yoke 106, may result in angle α increasing and movement of second pivot pin 120 downwards, toward handle 102, may result in angel α decreasing.

In some embodiments, handle 102 includes slot 122. In some embodiments, second pivot pin 120 is disposed through slot 122 thereby coupling handle 102 to pivot assembly 115. Slot 122 may receive second pivot pin 120 such that second pivot pin 120 is able to move within slot 122. For example, second pivot pin 120 may slide within slot 122. Second pivot pin 120 may be configured to slide proximally and distally within slot 122. In some embodiments, second pivot pin 120 disposed within slot 122 is the point load where the gripping force applied to handle 102 is translated to axial movement of yoke 106 and thus actuation of instrument assembly 171. For example, the gripping force applied to handle 102 to move handle 102 from the initial position to the actuated position may result in driving second pivot pin 120 distally within slot 122. Slot 122 may be shaped such that when second pivot pin 120 is driven distally within slot 122, second pivot pin 120 is driven upwards towards yoke 106, which drives first link 114 and yoke 106 distally. Yoke 106 being driving distally may result in actuation of instrument assembly 171.

Figure 7:
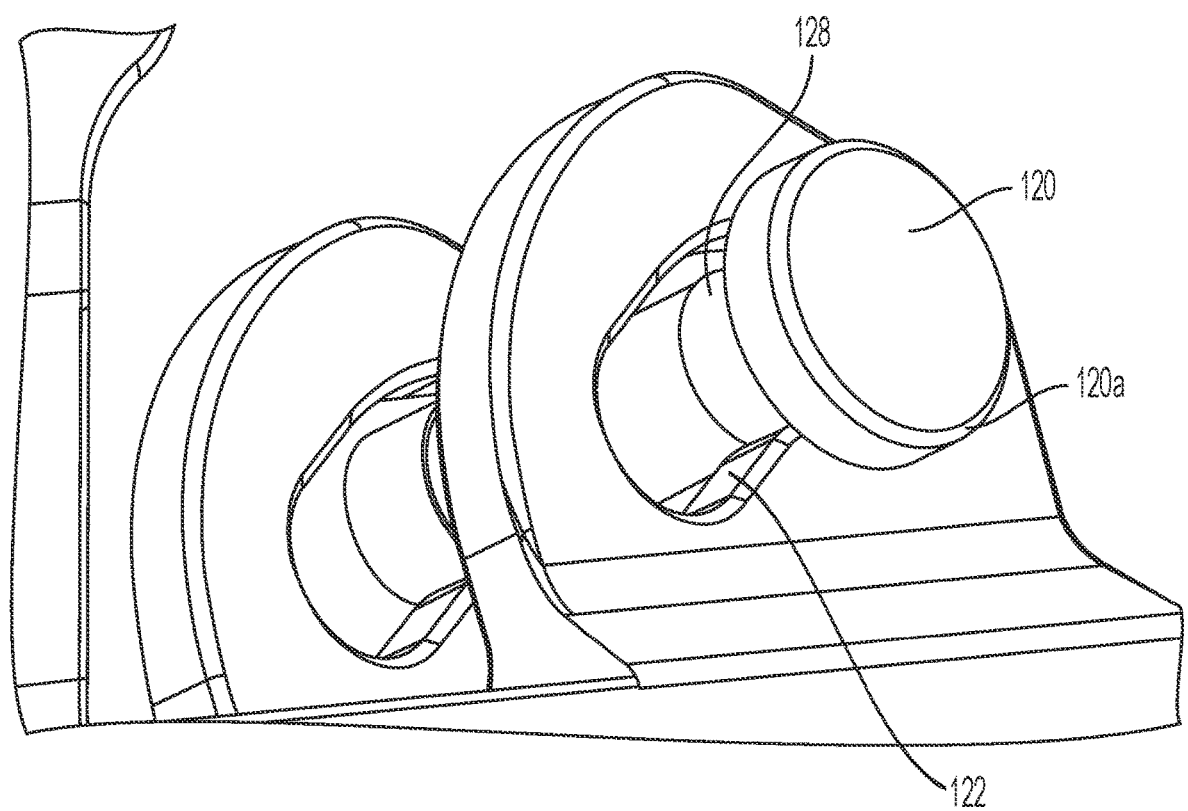
FIG. 7 is a perspective view of an exemplary ring disposed around a pivot pin of the surgical tool of FIG. 4A.

Referring to FIGS. 4A-4B and 7, slot 122 may be curved and elliptical in shape. However, slot 122 may be rectangular, triangular, polygonal, or any other shaped desired. In one embodiment, slot 122 is curved downward towards handle 102. In some embodiments, slot 122 being curved downward towards handle 102 results in an increase in the force efficiency when handle 102 is proximate the actuated position. For example, when slot 122 is curved downward, as user actuates handle 102, the gripping force required decreases as handle 102 moves to the actuated position. Slot 122 being curved downward towards handle 102 may result in a decrease in gripping force required to keep handle 102 in the actuated position compared to slot 122 not being curved downward. In an alternative embodiment, slot 122 is curved upward towards yoke 106. In some embodiments, slot 122 being curved upward towards yoke 106 results in an increase in the force efficiency when handle 102 is proximate the initial position. For example, when slot 122 is curved upward, as user actuates handle 102, the gripping force required at the beginning of actuating handle 102 is decreased compared to the gripping forced required to keep handle 102 in the actuated position.

Slot 122 may have proximal end 122a and distal end 122b. In some embodiments, proximal end 122a of slot 122 may be disposed above distal end 122b of slot 122, such that proximal end 122a is disposed closer to yoke 106 than distal end 122b. In some embodiments, slot 122 is curved and has radius of curvature R. In some embodiments, the larger the radius of curvature R is when slot 122 is curved downward towards handle 102, the less gripping force required on handle 102 to keep handle 102 in the actuated position due to the curved shape of slot 122. For example, slot 122 having a downward shape and a radius of curvature R of approximately 20 mm may result in approximately 7.5% reduction of force compared to slot 122 having a radius of curvature R of approximately 5 mm. In some embodiments, a very large radius of curvature R of slot 122 may result in a significant gripping force to move handle 102 out of the initial position, but very minimal force to move handle 102 to the actuated position and keep handle 102 in the actuated position.

In some embodiments, slot 122 is sized and shaped such that second pivot pin 120 is slidable within slot 122. For example, second pivot pin 120 may be configured to slide between proximal end 122a and distal end 122b. In some embodiments, second pivot pin 120 may include end 120a, which may be sized to prevent second pivot pin 120 from inadvertently exiting slot 122. For example, end 120a of second pivot pin 120 may be sized to have a diameter greater than the width of slot 122 to prevent second pivot pin 120 from inadvertently being removed from slot 122.

Referring to FIGS. 4A-4B, actuation of handle 102 may result in second pivot pin 120 sliding within slot 122. For example, actuation of handle 102 from the initial position (FIG. 4A) to the actuated position (FIG. 4B) may result in second pivot pin 120 sliding from proximal end 122a to distal end 122b of slot 122. In some embodiments, when handle 102 is in the initial position, second pivot pin 120 is disposed proximate proximal end 122a of slot 122 and when handle 102 is in the actuated position, second pivot pin 120 is disposed proximate distal end 122b of slot 122.

In some embodiments, movement of handle 102 from the initial position to the actuated position results in angle α increasing due to second pivot pin 120 sliding within slot 122. For example, when handle 102 is in the initial position angel α may be 110° and when handle 102 is in the actuated position angel α may be 160°. When angle α increases due to movement of second pivot pin 120 within slot 122 of handle 102, second link 118 rotates about third pivot pin 112 and drives third pivot pin 112 towards distal end 103, thereby pushing out/actuating yoke 106 towards distal end 103. In contrast, decreasing angle α results in second link 118 and third pivot pin 112 moving towards proximal end 105, and thus pulling yoke 106 towards proximal end 105. Increasing or decreasing of angel α is caused by movement of second pivot pin 120 within slot 122, which is due to movement of handle 102. In some embodiments, first link 114 and second link 118 pivot about second pivot pin 120. In some embodiments, movement of second pivot pin 120 results in translation of yoke 106 proximally and distally, thereby causing actuation of instrument assembly 171. For example, handle 102 moving from the initial position to the actuated position may result in second pivot pin 120 move towards yoke 106, increasing angel α and driving yoke 106 towards distal end 103. Driving yoke 106 towards distal end 103 may actuate instrument assembly 171, which may be a grasping instrument, causing jaw 173 to close.

In practice, when handle 102 moves from the initial position to the actuated position, handle 102 pivots about pivot point 108 and second pivot pin 120. Handle 102 pivoting about second pivot pin 120 results in second pivot pin 120 sliding within slot 122 distally and moving upwards towards yoke 106, which increases angle α and pushes second link 118 towards distal end 103. Increasing of angle α and pushing out of second link 118 towards distal end 103 pushes out third pivot pin 112 and drives yoke 106 forward towards distal end 103. In some embodiments, driving yoke 106 towards distal end 103 results in actuating of instrument assembly 171, such as a grasping instrument. In other words, when handle 102 is moved from the initial position to the actuated position, yoke 106 is driven towards distal end 103 via pivot assembly 115, which actuates instrument assembly 171.

In some embodiments, tool 100 is used in conjunction with robotic surgical devices for robotic surgeries and includes a motor. The motor may be configured to drive second pivot pin 120. For example, instead of handle 102, a motor may be used to drive second pivot pin 120 up and towards yoke 106, thereby driving yoke 106 towards distal end 103. The motor may be coupled to a robotic surgical device and may be controlled by a user. In some embodiments, a user may actuate the motor, which causes movement of second pivot pin 120, thereby driving yoke 106 towards distal end 103 and actuating instrument assembly 171.

Figure 6A:
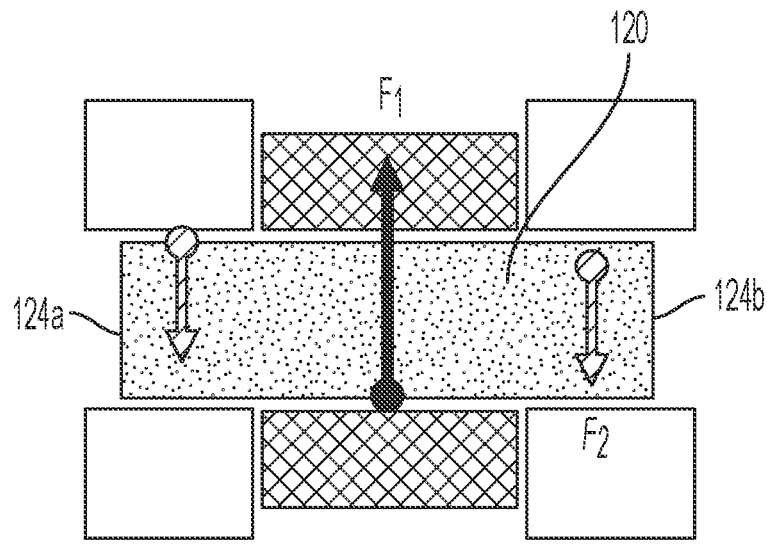
FIG. 6A is a schematic view of an exemplary pivot pin of the surgical tool of FIG. 4A.
Figure 6B:
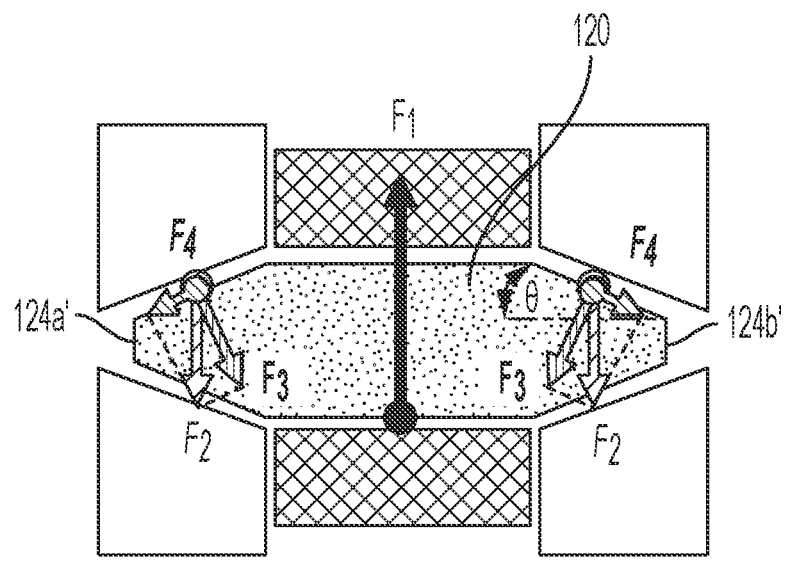
FIG. 6B is a schematic view of an alternative exemplary pivot pin of the surgical tool of FIG. 4A.

Referring to FIGS. 6A and 6B, second pivot pin 120 may have first end 124a and second end 124b. First end 124a and second end 124b may be portions of second pivot pin 120 that contact slot 122. In some embodiments, first end 124a and second end 124b are flat and non-tapered. However, first end 124a and second end 124b being non-tapered may result in considerable frictional force between second pivot pin 120 and slot 122. In some embodiments, to reduce the amount of frictional force between second pivot pin 120 and slot 122, second pivot pin 120 may include first end 124a' and second end 124b', which are tapered. First end 124a' and second end 124b' being tapered decreases the perpendicular force felt on first end 124a' and second end 124b' by slot 122. Further, first end 124a' and second end 124b' being tapered may decrease the frictional force between second pivot pin 120 and slot 122 when second pivot pin 120 slides within slot 122. In some embodiments, second pivot pin 120 may taper from a diameter of approximately 4 mm to a diameter of approximately 2 mm.

Referring to FIG. 7, second pivot pin 120 may include one or more rings 128. Ring 128 may be a low friction ring disposed around the circumference of second pivot pin 120 to reduce the amount of friction between slot 122 and second pivot pin 120. In some embodiments, second pivot pin 120 may include ring 128 proximate first end 124a or 124a' and/or proximate second end 124b or 124b'. However, second pivot pin 120 may include ring 128 at any location. For example, second pivot pin 120 may include ring 128 across the entire exterior surface or may include ring 128 only where second pivot pin 120 contacts slot 122. In some embodiments, one or more of first pivot pin 116, second pivot pin 120, and third pivot pin 112 includes one or more rings 128.

Figure 8:
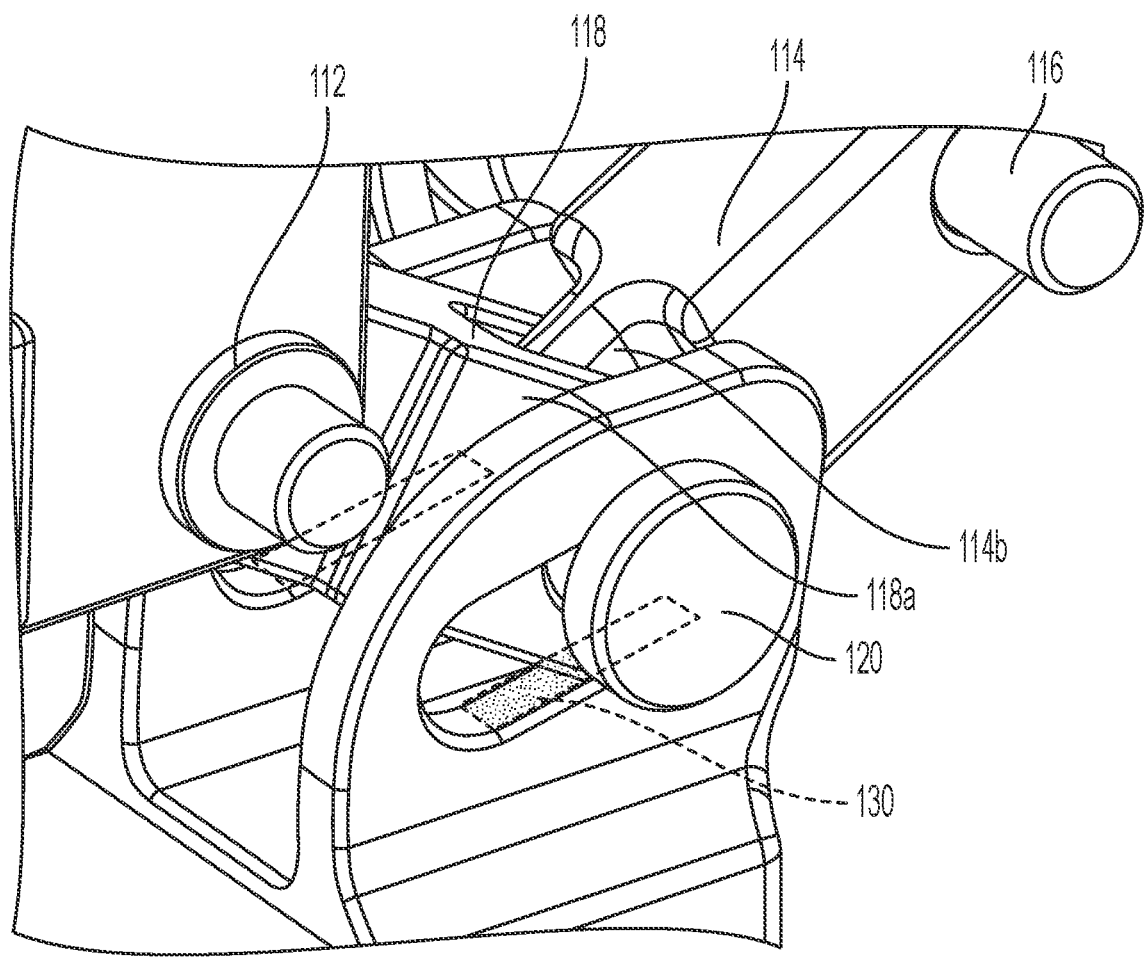
FIG. 8 is a perspective view of the pivot assembly of FIG. 4A showing an exemplary low-friction coating applied to a slot that receives a pivot pin.

Referring to FIG. 8, slot 122 may include coating 130, which may be a low-friction coating. Coating 130 may be applied within the interior surface of slot 122. For example, coating 130 may be applied to the portion of slot 122 that contacts second pivot pin 120. Coating 130 may be applied to slot 122 during manufacturing of tool 100. Coating 130 may be a substance that is coated on the interior of slot 122 or may be a material coupled to the interior of slot 122. For example, coating 130 may be a low-friction primer applied to the interior of slot 122 or coating 130 may be a low-friction strip of material coupled to the interior of slot 122 by, for example, an adhesive. Coating 130 may be PTFE. Coating 130 may be applied to a portion of slot 122 or the entirety of slot 122. For example, coating 130 may be interspersed within slot 122 or may cover the entirety of slot 122. In some embodiments, coating 130 is applied to any locations where first pivot pin 116, second pivot pin 120, and/or third pivot pin 112 contacts a surface.

Figure 9:
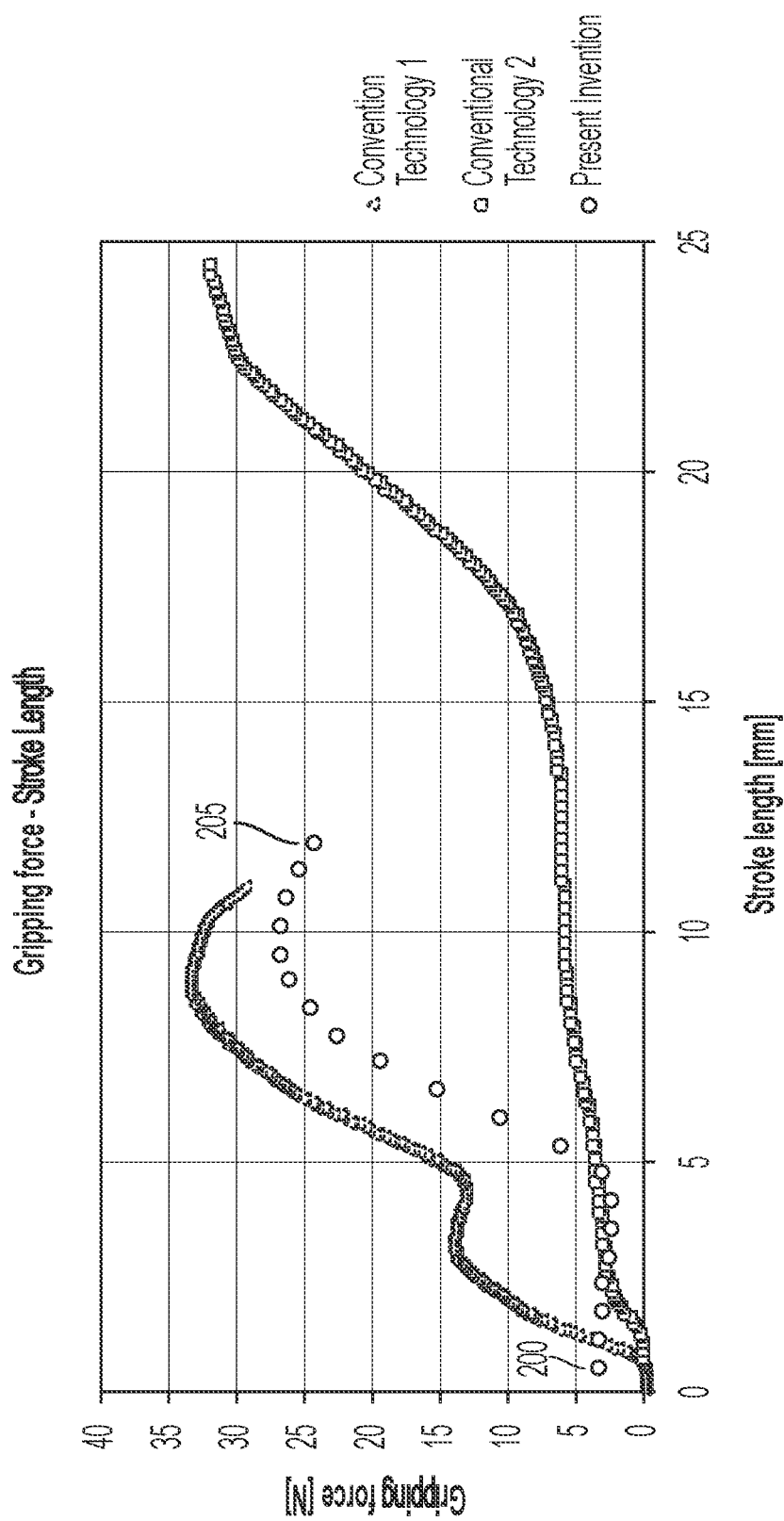
FIG. 9 is a graph illustrating the required actuation gripping force over the stroke length of the handle of an exemplary embodiment of the present invention and the prior art.

Referring to FIG. 9, a graph is provided illustrating the gripping force required to achieve the desired stroke length. For the present invention sample, the graph in FIG. 9 shows the gripping force [N] as the stroke length [mm] changes in the process of handle 102 transitioning from the initial position illustrated in FIG. 4A (corresponding to location 200 in FIG. 9) to the actuated position illustrated in FIG. 4B (corresponding to location 205 in FIG. 9). As shown in the graph, tool 100 may require less of a gripping force to reach the desired stroke volume compared to other prior art tools, such as Conventional Technology 1 and Conventional Technology 2. For example, tool 100 allows for the maximum gripping force to actuate handle 102 to be less than 35 N and the stroke length of handle 102 to be less than 14 mm. This results in an approximately 10% decrease in the maximum gripping force required to actuate handle 102 compared to other prior art tools.

In practice, the smaller the gripping force and the shorter the stroke length, the less fatigue a user will experience when using tool 100. Further, users with small hands or weak hands may not be able to actuate handle 102 if the maximum gripping force required to actuate handle 102 is greater than 35 N. However, handle 102 having a stroke length too short will result in difficultly performing delicate operations with tool 100 and using instrument assembly 171 in confined spaces. Therefore, handle 102 having a maximum gripping force less than 35 N and a stroke length less than 14 mm allows the user to maintain a grip on handle 102 to operate tool 100, resulting in less fatigue compared to other prior art tools, such as Conventional Technology 1 and Conventional Technology 2. The force measured in the graph of FIG. 9 occur when no tissue or objects are being grasped by instrument assembly 171.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

What is claimed is:

1. A surgical tool comprising:
   a housing having a proximal end and a distal end;
   a yoke disposed within the housing between the proximal end and the distal end;
   a handle pivotally coupled to the housing;
   a pivot assembly coupling the yoke to the housing, the pivot assembly including a first link having a first end and a second end, the first end of the first link rotatably coupled to the housing and the second end of the first link rotatably coupled to a second link at a first end of the second link, the second link having a second end rotatably coupled to the yoke; and
   a pivot pin pivotably coupling the second end of the first link to the first end of the second link, wherein the pivot pin is disposed through the handle, the first link, and the second link; and
   a slot disposed within in the handle configured to slidably receive the pivot pin,
   wherein the handle is coupled to the pivot assembly such that movement of the handle causes movement of the yoke.

2. The surgical tool of claim 1, wherein the slot includes a proximal end and a distal end, the pivot pin being proximate to the proximal end of the slot when the handle is in an initial position and the pivot pin being proximate the distal end of the slot when the handle is in an actuated position.

3. The surgical tool of claim 2, wherein the proximal end of the slot is disposed above the distal end of the slot.

4. The surgical tool of claim 2, wherein the slot is curved and extends from the proximal end of the slot to the distal end of the slot.

5. The surgical tool of claim 2, wherein the slot is downwardly curved towards the handle.

6. The surgical tool of claim 2, wherein the slot is upwardly curved towards the yoke.

7. The surgical tool of claim 1, wherein the pivot pin includes a ring contacting an inner surface of the slot.

8. The surgical tool of claim 1, wherein the slot includes a low-friction coating formed on a region of the slot where the pivot pin contacts the slot.

9. The surgical tool of claim 1, wherein the pivot pin includes a first end and a second end, each of the first end and the second end being tapered.

10. The surgical tool of claim 1, wherein the handle is coupled to the housing at a pivot point, the pivot pin being disposed closer to a bottom of the handle than the pivot point.

11. The surgical tool of claim 1, wherein the pivot pin is disposed between the first link and the second link.

12. The surgical tool of claim 1, wherein the first link and the second link form an angle, the angle increasing as the yoke moves towards the distal end.

13. The surgical tool of claim 1 further comprising:
    a grasper instrument disposed at a distal end of the housing, wherein movement of the handle results in movement of the yoke causing actuation of the grasper instrument.

14. The surgical tool of claim 1, wherein the first link is disposed distal to the second link.

15. The surgical tool of claim 1, wherein the handle is coupled to one or both of the first link and the second link.

16. The surgical tool of claim 1, wherein the second end of the first link is rotatably coupled to the first end of the second link by a pivot pin disposed through the handle.

17. The surgical tool of claim 1, wherein the second end of the second link is rotatably coupled to the yoke by a second pivot pin disposed through the yoke.

* * * * *